United States Patent [19]

Lomas

[11] Patent Number: 5,542,128
[45] Date of Patent: Aug. 6, 1996

[54] HEADWEAR FOR SUPPORTING A BREATHING APPARATUS

[76] Inventor: Christiane Lomas, 23/30 Dutruc Street, Randwick NSW 2031, Australia

[21] Appl. No.: 229,917

[22] Filed: Apr. 19, 1994

[30] Foreign Application Priority Data

Apr. 20, 1993 [AU] Australia .................................. PL8358

[51] Int. Cl.⁶ ...................................................... A42B 1/04
[52] U.S. Cl. ............................ 2/173; 2/171.2; 2/209.13; 128/207.11; 128/207.17
[58] Field of Search ............................. 2/6.2, 171, 171.2, 2/171.3, 173, 202, 207, 209.13, 422, 418, 417, 195.2, 195.3; 602/65, 74; 604/305; 606/204.15; 128/207.11, 207.17, 201.22, 205.25

[56] References Cited

U.S. PATENT DOCUMENTS 1,706,601  3/1929  Drager ............................... 128/207.11
5,361,416  11/1994  Petrie et al. ................................. 2/171

FOREIGN PATENT DOCUMENTS 1259571  3/1960  France ..................................... 2/195.2

Primary Examiner—Diana Biefeld
Attorney, Agent, or Firm—Amster, Rothstein & Ebenstein

[57] ABSTRACT

A hood or cap for a face mask breathing apparatus formed of flexible material having a narrow front piece which extends down the forehead of the wearer adjacent the nostril which merges into a wider back piece to encompass at least the rear of the head and the rear of the neck of the wearer the front piece and back piece being provided with straps to connect the hood to a face mask and correctly position and maintain the mask on the face of the wearer.

12 Claims, 3 Drawing Sheets

HEADWEAR FOR SUPPORTING A BREATHING APPARATUS

This invention relates to hoods or caps for use with breathing apparatus or face masks and whilst it has been primarily developed for use with breathing apparatus for medical purposes, it also finds application for use with breathing apparatus for industrial use.

In one particular known application the mask comprises a housing formed of two halves, one half is provided with means whereby the housing can be connected to an air or gas supply (hereafter referred to as air supply) and the other half comprises a nose piece which in use is adapted to encompass the nostril of the wearer. The mask is maintained on the face of the wearer by a harness comprising two straps, one of which is connected to each side of the mask and extends transversely around the neck of the wearer and the other of which is connected by one end to the top of the mask, passes upwards medially over the head of the wearer and is attached by its free end to the transverse strap.

This method of attaching the mask to the wearer is unstable and the mask can be and is frequently dislodged from its correct position on the wearer.

If the mask is dislodged it can lead to a breakdown in air supply to the wearer which in the case of medical application can be dangerous.

The present invention provides a hood or cap for use with air masks, which is relatively inexpensive, comfortable to wear, and which effectively maintains the mask correctly positioned on the face of the wearer thereby ensuring a steady and uninterrupted flow of air to the wearer.

The invention in its broadest form comprises a hood of flexible material for a face mask, the hood having a narrow front piece adapted to extend down the forehead of the wearer adjacent the nostril and merging into a wider back piece to encompass at least the rear of the head and the rear of the neck of the wearer, said hood being provided with transverse and vertical connection means whereby the hood is connected to a face mask to correctly position and maintain the mask on the face of the wearer.

Preferably, (a) the connecting means are adjustable as to length;

(b) the back piece is provided with a medial slit extending from its bottom edge towards the said front piece and connection means are provided to connect opposite edges of the slit whereby the width of the back piece can be adjusted to conform with the head of the wearer and to facilitate the positioning and removal of the face mask from the wearer;

(c) the hood is formed of non-elastic fabric (e.g. cotton) and the fabric is cut so that the warp threads are parallel to the axis of the transverse connection means and the weft threads are parallel to the axis of the from piece.

The hood is formed of two substantially crescent shaped halves having a concave edge and a convex edge, the convex edges of the respective halves when secured together form an apex at one end, thereby providing a narrow front piece adapted to extend down the forehead of the wearer adjacent the nostril, the apex having connection means whereby the hood is vertically connected to a face mask, said crescent shaped halves merging into a wider back piece having a bottom edge and adapted to encompass at least the rear of the head and the rear of the neck of the wearer, the concave edge of each of said halves and said bottom edge merging into a transversely extending arm provided with connection means whereby the hood can be connected to each side of said face mask.

In certain cases a medial slit extends from the bottom edge of the hood between the convex edges towards the apex, opposed edges of the slit being provided with connection means whereby the width of the back piece can be adjusted to facilitate the fitting and removal of the face mask after it has been size fitted to accommodate a particular wearer.

Preferred embodiments of the invention will now be described with reference to the accompanying drawings in which.

Figure 1:
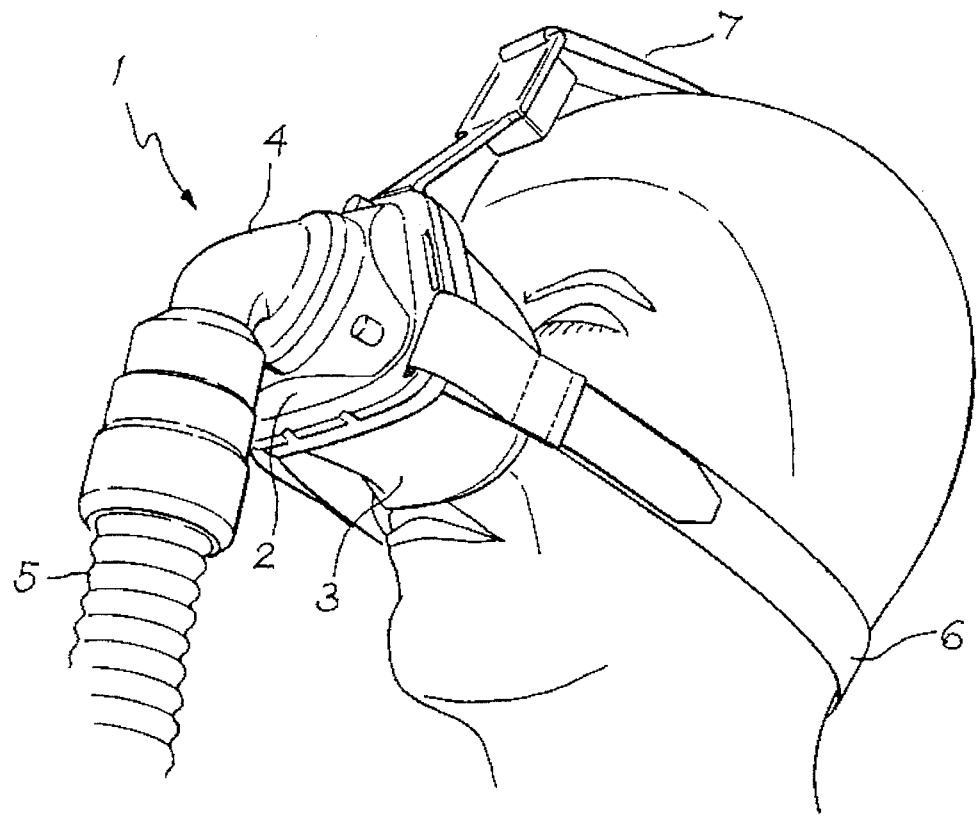
FIG. 1 is a perspective view of a typical face mask showing a known harness whereby it is connected to a wearer.
Figure 2:
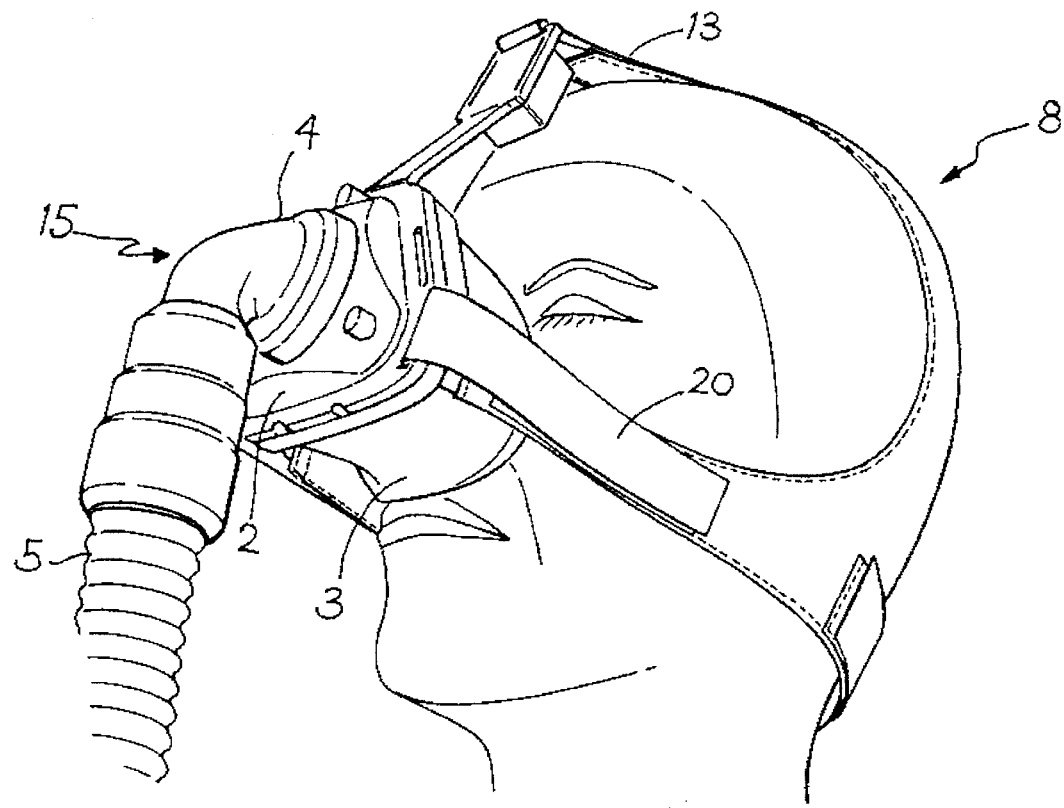
FIG. 2 is a perspective view of a typical face mask fitted with a hood in accordance with the invention.
Figure 3:
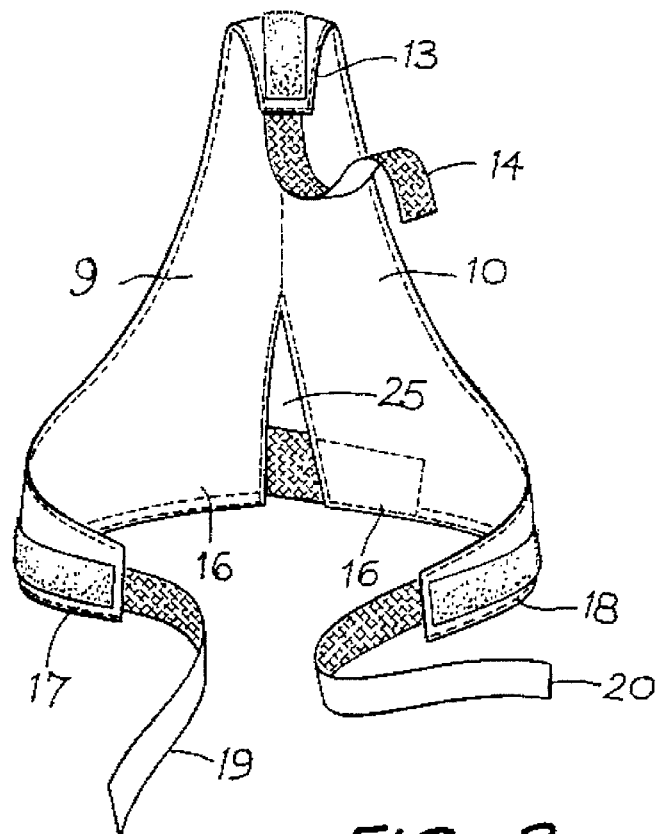
FIG. 3 is a rear view of the hood in accordance with the invention.
Figure 4:
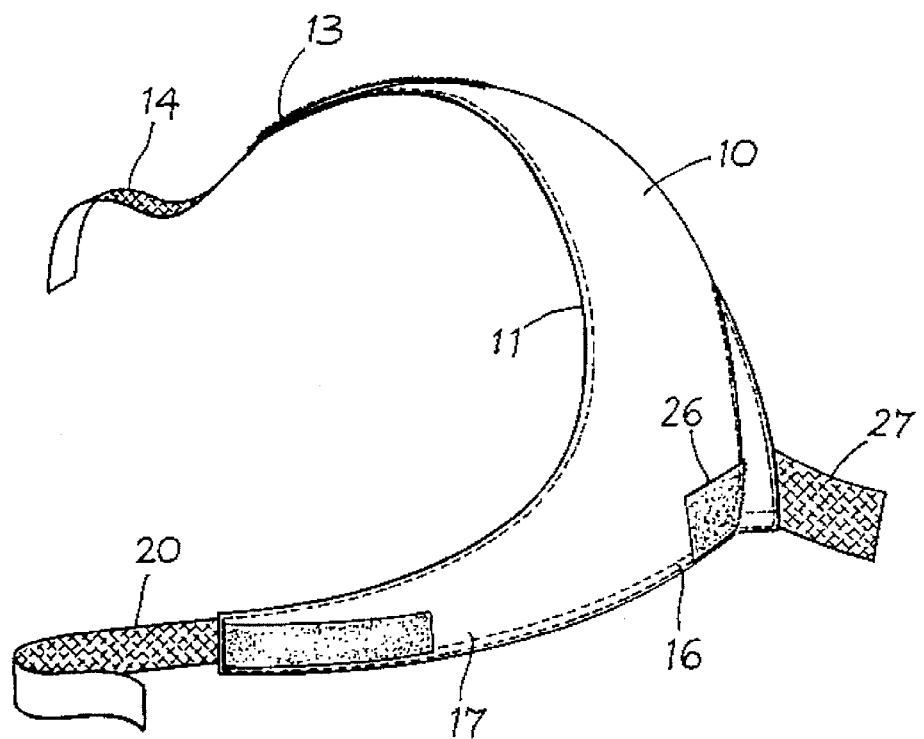
FIG. 4 is a side view of FIG. 3.
Figure 5:
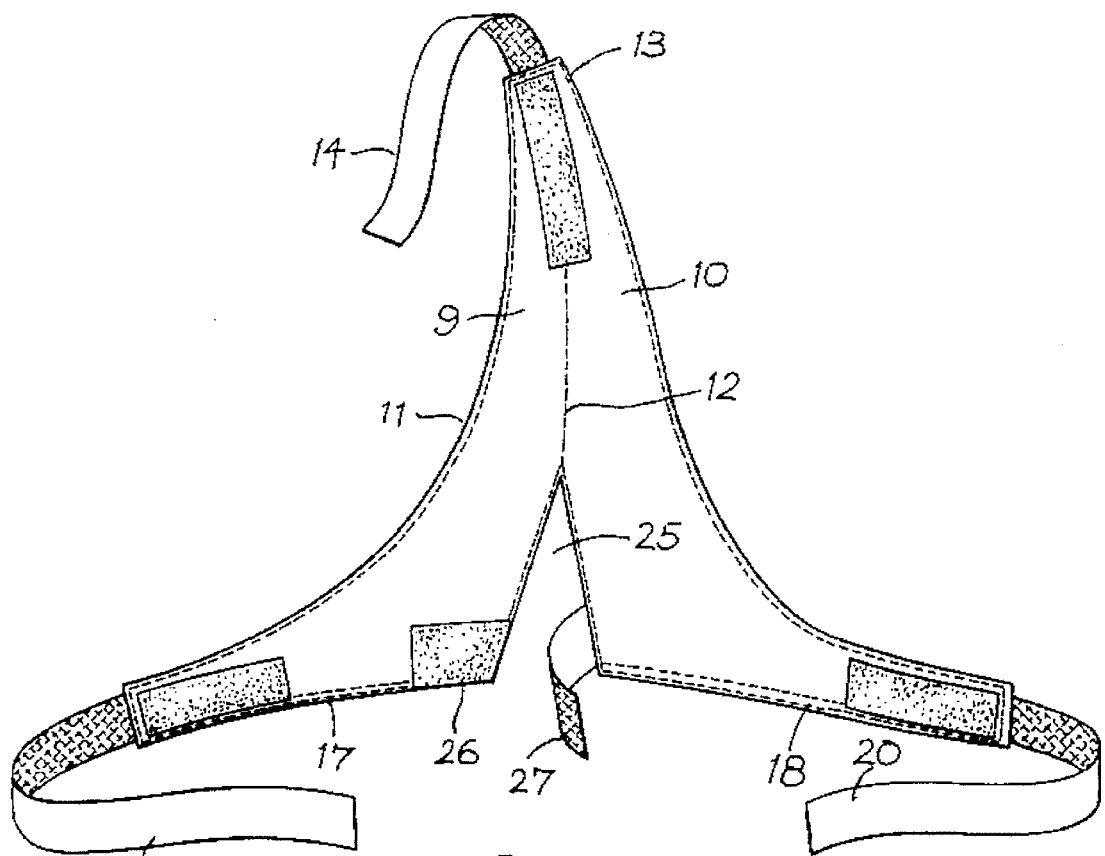
FIG. 5 is a front view of FIG. 3.
Figure 6:
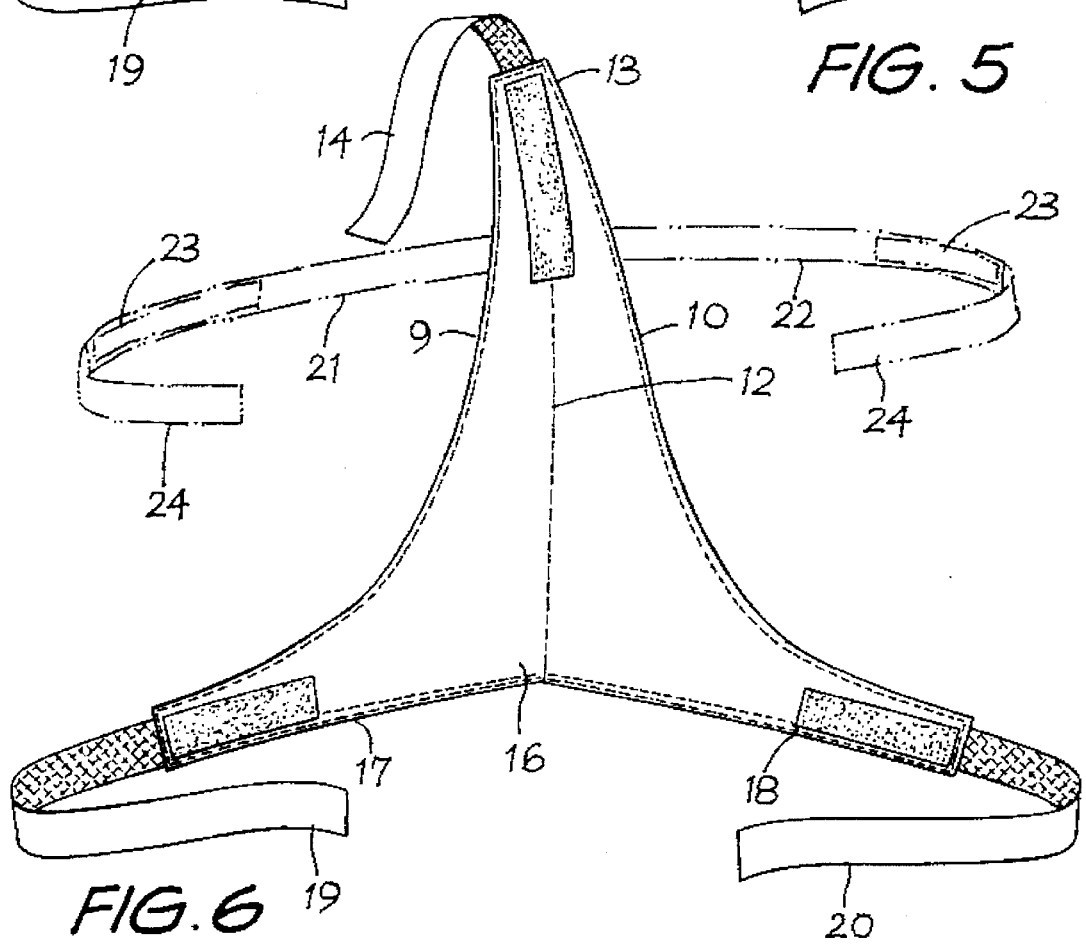
FIG. 6 is a rear view of a modified form of the hood.

Referring now to the drawings.

FIG. 1 illustrates a typical face mask with a conventional harness. The face mask designated by the reference 1 comprises a housing formed of two halves 2 and 3, one half 2 is provided with means 4 whereby the housing is connected to an air supply 5. The other half 3 comprises a nose piece which is adapted to encompass the nostril of the wearer.

The mask 1 is maintained on the face of the wearer, by an elasticised harness comprising a strap 6 connected to each side of the mask and a strap 7 connected to the top of the mask and medially to the transverse strap 6 at the back thereof.

It will be apparent that the harness arrangement is relatively unstable. It depends on a firm positioning of the nose piece 3 and the harness arrangement to maintain the face mask in position. Experience has shown that a harness of this type can easily move on the wearer with the result the nose face is not maintained correctly in position. When this happens the air supply to the wearer is reduced caused by air leakage or is interrupted altogether.

Referring now to FIGS. 2 to 6 in which like parts are identified by the same reference numerals.

The hood designated generally by the reference 8 is formed of two substantially crescent shaped halves 9 and 10 having a concave edge 11 and a convex edge 12.

The convex edges 12 are secured together to form an apex 13 at one end thereby providing a narrow front piece as illustrated in FIGS. 2 to 6 which extends down the forehead of the wear adjacent the nostril. The apex having connection means 14 whereby it is connected to the top edge of a face mask 15.

The crescent shaped halves 9 and 10 merge into a wider back piece 16 to encompass at least the rear of the head and the rear of the neck of the wearer. The other end of each of the halves 9 and 10 merges into transversely extending arms 17 and 18 provided with connection means 19 and 20 whereby the hood 8 can be connected to each side of the face mask 15.

In certain cases additional arms 21 and 22 (see FIG. 6) extend from the concave edge 11 of each half which are provided with connection means 23 and 24 to which also connect these arms to the face mask 15 to provide additional support for the face mask on the face of the wearer.

In some applications the back piece 16 is provided with a medial slit 25, the free ends of which are provided with connection means 26 and 27 whereby the width of the back piece can be adjusted to conform the hood to the shape of the head of the wearer. The slit also facilitates the rapid fitting and removal of the face mask from the wearer.

The hood is preferably made from non-elastic fabric (e.g. cotton) and the fabric is cut and the hood assembled so that the warp threads are positioned to be parallel to the axes of the arms 17 and 18 and the weft threads are normal to the axes of the warp threads.

By this arrangement the hood is practically unstretchable which is an important factor in the reduction of air leakage from the mask. The shape of the hood stabilises the position of the bottom edge of the back piece. Cranial shift of the headgear is eliminated by the friction between the fabric and the head and by the pulling effect of the side connection means, which tends to pull the lower edge of the headgear caudally because of the shape of the head and the neck caudal to the occipital protuberance. Therefore, the only caudal bending of the mask is allowed by the mask itself and by the minor stretching of the transverse strap.

The large total area of the hood spreads the forces on the connection means to a large area of the head and neck. The force spreading makes the mask and the hood more comfortable to wear.

The back opening of the hood provided by the slit 25 secured by the connection means 26 and 27 provides means whereby when the hood is sized fitted to the shape of the head of the wearer, it can be quickly placed on and removed from the head without further adjustment.

The connection means are preferably made of or include a multitude of minihook and miniloop connections.

I claim:

1. A hood of flexible material for use with a face mask, said hood being formed of two halves of substantially crescent shape having a concave edge and a convex edge, the convex edges of the respective halves being secured together to form an apex at one end providing a narrow front piece adapted to extend over the top of the head of a wearer and having a front edge extending towards the forehead of a wearer adjacent the nostrils, the convex and concave edges of each of said halves and said front edge merging into a longitudinally extending arm having vertical connection means whereby the hood is vertically connectable to the top of the face mask, said halves merging into a wider back piece having a bottom edge to encompass at least the rear of the head and the rear of the neck of a wearer, the hood being provided with transverse connection means whereby the hood is connectable to each side of the face mask.

2. A hood as claimed in claim 1 including means for adjusting the effective length of the connection means.

3. A hood as claimed in claim 2 wherein the connection means comprise multiple minihook and miniloop fasteners.

4. A hood as claimed in claim 1 wherein the back piece is provided with a medial slit extending from its bottom edge towards said front piece and connection means are provided which connect opposite edges of the slit whereby the width of the back piece can be adjusted to conform with the head of the wearer to facilitate the positioning and removal of the face mask from a wearer.

5. A hood as claimed in claim 4 wherein the connection means comprise multiple minihook and miniloop fasteners.

6. A hood as claimed in claim 1 wherein the hood is formed of non-elastic fabric wherein the warp threads are parallel to the transverse connection means and the weft threads are normal to the warp threads.

7. A hood of flexible material for use with a face mask, said hood being formed of two halves of substantially crescent shape having a concave edge and a convex edge, the convex edges of the respective halves being secured together to form an apex at one end providing a narrow front piece adapted to extend towards the forehead of a wearer adjacent the nostrils, said apex having connection means whereby the hood is vertically connectable to the face mask, said halves merging into a wider back piece having a bottom edge to encompass at least the rear of the head and the rear of the neck of a wearer, the concave edge of each of said halves and said bottom edge merging into transversely extending arms having connection means whereby the hood is connectable to each side of the face mask.

8. A hood as claimed in claim 7 including means for adjusting the effective length of the connection means.

9. A hood as claimed in claim 8 wherein the connection means comprise multiple minihook and miniloop fasteners.

10. A hood as claimed in claim 7 wherein the back piece is provided with a medial slit extending from its bottom edge towards said front piece and connection means are provided which connect opposite edges of the slit whereby the width of the back piece can be adjusted to conform with the shape of the head of the wearer to facilitate the positioning and removal of the face mask from a wearer.

11. A hood as claimed in claim 10 wherein the connection means comprises multiple minihook and miniloop fasteners.

12. A hood as claimed in claim 7 wherein the hood is formed of non-elastic fabric wherein the warp threads are parallel to the transverse connection means and the weft threads are normal to the warp threads.

* * * * *